US006607912B2

United States Patent
Blissard et al.

(10) Patent No.: US 6,607,912 B2
(45) Date of Patent: Aug. 19, 2003

(54) GP64-NULL BACULOVIRUSES PSEUDOTYPED WITH HETEROLOGOUS ENVELOPE PROTEINS

(75) Inventors: Gary W. Blissard, Ithaca, NY (US); Jodie T. Mangor, Ithaca, NY (US); Scott A. Monsma, Mdison, WI (US)

(73) Assignee: Boyce Thompson Institute for Plant Research, Inc., Ithaca, NY (US)

( * ) Notice: Subject to any disclaimer, the term of this patent is extended or adjusted under 35 U.S.C. 154(b) by 0 days.

(21) Appl. No.: 09/925,365

(22) Filed: Aug. 9, 2001

(65) Prior Publication Data

US 2002/0115188 A1 Aug. 22, 2002

Related U.S. Application Data

(60) Provisional application No. 60/224,612, filed on Aug. 11, 2000.

(51) Int. Cl.[7] ............... C12N 15/866; C12N 15/63; C12N 15/64
(52) U.S. Cl. ............ 435/320.1; 435/325; 435/366; 435/455; 435/456; 435/69.1; 435/348; 424/93.1; 424/93.2; 424/93.6
(58) Field of Search ............... 435/320.1, 325, 435/366, 455, 456, 69.1, 348, 235.1; 424/93.1, 93.2, 93.6

(56) References Cited

U.S. PATENT DOCUMENTS 5,750,383 A * 5/1998 Blissard et al. .......... 435/172.3

FOREIGN PATENT DOCUMENTS

| WO | WO 98/11243 | 3/1998 |
|---|---|---|
| WO | WO 99/09193 | 2/1999 |
| WO | WO 00/05394 | 2/2000 |

OTHER PUBLICATIONS

Kmiec, E.B., American Scientist, 1999, vol. 87, pp. 240–247.*

Paillard, F., Human Gene Therapy, 1998, vol. 9, pp. 767–770.*

Verma et al., Nature, 1997, vol. 389, pp. 239–242.*

Fox, J. L., Nature Biotechnology, 2000, vol. 18, pp. 143–144.*

Anderson, W. French, Nature, 1998, vol. 392, pp. 25–30.*

Barsoum et al. "Efficient Transduction of Mammalian Cells by a Recombinant Baculovirus Having the Vesicular Stomatitis Virus G Glycoprotein." Human Gene Therapy, XX, XX, vol. 8, No. 17, Nov. 20, 1997, p. 2011–2018.

Boublik, Yven et al. "Eukaryotic Virus Display: Engineering the Major Surface Glycoprotein of the Autographa Californica Nuclear Polyhedrosis Virus (AcNPV) for the Presentation of Foreign Proteins on the Virus Surface." Biotechnology. vol. 13. Oct. 1995. p. 1079–1084.

Mangor, J.T. et al. "A GP54–Null Baculovirus Pseudotyped with Vesicular Stomatitis Virus G Protein." Journal of Virology, Mar. 2001. P. 2544–2556.

* cited by examiner

Primary Examiner—David Guzo
(74) Attorney, Agent, or Firm—Brown & Michaels, PC

(57) ABSTRACT

A pseudotyped baculovirus comprises a deletion, inactivation or reduction from regulation of a baculovirus envelope protein gene, and is engineered to express an envelope protein from another virus or cell, or another protein or molecule that facilitates entry of said baculovirus into a non-host cell, or provided with a heterologous envelope protein or another protein or molecule that facilitates entry of said baculovirus into a non-host cell by other suitable means. Such baculoviruses can be used to efficiently deliver genes to mammalian cells or organisms, and such genes can be expressed either from the baculovirus genome, or integrated into the mammalian cell genome, and can be used for expression of proteins such that purification of secreted or other protein products does not require removal of contaminating baculovirus particles or baculovirus envelope proteins.

15 Claims, 2 Drawing Sheets

SEQUENCE LISTING

<160> NUMBER OF SEQ ID NOS: 18

<210> SEQ ID NO 1
<211> LENGTH: 21
<212> TYPE: DNA
<213> ORGANISM: Vesicular stomatitis virus

<400> SEQUENCE: 1
tccgatcctt cactccatct g                                            21

<210> SEQ ID NO 2
<211> LENGTH: 21
<212> TYPE: DNA
<213> ORGANISM: Vesicular stomatitis virus

<400> SEQUENCE: 2
tagctgagat ccactggaga g                                            21

<210> SEQ ID NO 3
<211> LENGTH: 21
<212> TYPE: DNA
<213> ORGANISM: Autographa californica nucleopolyhedrovirus

<400> SEQUENCE: 3
gttgttattg gctacaaggg c                                           21

<210> SEQ ID NO 4
<211> LENGTH: 22
<212> TYPE: DNA
<213> ORGANISM: Autographa californica nucleopolyhedrovirus

<400> SEQUENCE: 4
tgagtagagc gtggcgttga gc                                          22

<210> SEQ ID NO 5
<211> LENGTH: 30
<212> TYPE: DNA
<213> ORGANISM: Autographa californica nucleopolyhedrovirus

<400> SEQUENCE: 5
cagaattcat gtgtgtaatt tttccggtag                                  30

<210> SEQ ID NO 6
<211> LENGTH: 35
<212> TYPE: DNA
<213> ORGANISM: Autographa californica nucleopolyhedrovirus

<400> SEQUENCE: 6
aatgctctag attatttaat tgtgtttaat attac                            35

<210> SEQ ID NO 7
<211> LENGTH: 34
<212> TYPE: DNA
<213> ORGANISM: Autographa californica nucleopolyhedrovirus

<400> SEQUENCE: 7
cgggatccaa tggcgctagt gcccgtgggt atgg                             34

<210> SEQ ID NO 8
<211> LENGTH: 34
<212> TYPE: DNA
<213> ORGANISM: Autographa californica nucleopolyhedrovirus

<400> SEQUENCE: 8
cgggatccgc gacggctatt cctccacctg cttc                             34

<210> SEQ ID NO 9
<211> LENGTH: 22
<212> TYPE: DNA
<213> ORGANISM: Autographa californica nucleopolyhedrovirus

<400> SEQUENCE: 9
tgcgtgttga agccgggatt tg                                          22

<210> SEQ ID NO 10
<211> LENGTH: 21
<212> TYPE: DNA
<213> ORGANISM: Autographa californica nucleopolyhedrovirus

<400> SEQUENCE: 10

-continued

```
gtcccgacag ctgggacgcc t                                              21

<210> SEQ ID NO 11
<211> LENGTH: 22
<212> TYPE: DNA
<213> ORGANISM: Autographa californica nucleopolyhedrovirus

<400> SEQUENCE: 11
cgaatggctg ttaccggtga cg                                             22

<210> SEQ ID NO 12
<211> LENGTH: 22
<212> TYPE: DNA
<213> ORGANISM: Autographa californica nucleopolyhedrovirus

<400> SEQUENCE: 12
ctcgctatac actcgcatgg ag                                             22

<210> SEQ ID NO 13
<211> LENGTH: 22
<212> TYPE: DNA
<213> ORGANISM: Autographa californica nucleopolyhedrovirus

<400> SEQUENCE: 13
cgatgcatat gtatggcata cc                                             22

<210> SEQ ID NO 14
<211> LENGTH: 23
<212> TYPE: DNA
<213> ORGANISM: Autographa californica nucleopolyhedrovirus

<400> SEQUENCE: 14
gagtttggga acaagtttga agg                                            23

<210> SEQ ID NO 15
<211> LENGTH: 22
<212> TYPE: DNA
<213> ORGANISM: Autographa californica nucleopolyhedrovirus

<400> SEQUENCE: 15
tgcgtgttga agccgggatt tg                                             22

<210> SEQ ID NO 16
<211> LENGTH: 22
<212> TYPE: DNA
<213> ORGANISM: Vesicular stomatitis virus

<400> SEQUENCE: 16
gtgaagagta tcagtgtgca tg                                             22

<210> SEQ ID NO 17
<211> LENGTH: 23
<212> TYPE: DNA
<213> ORGANISM: Vesicular stomatitis virus

<400> SEQUENCE: 17
gtagaaggtt ggttcagtag ttg                                            23

<210> SEQ ID NO 18
<211> LENGTH: 23
<212> TYPE: DNA
<213> ORGANISM: Autographa californica nucleopolyhedrovirus
```

-continued

<400> SEQUENCE: 18
gagtttggga acaagtttga agg 23

GP64-NULL BACULOVIRUSES PSEUDOTYPED WITH HETEROLOGOUS ENVELOPE PROTEINS

REFERENCE TO RELATED APPLICATIONS

This application claims an invention which was disclosed in Provisional Application No. 60/224,612, filed Aug. 11, 2000, entitled "A GP64-NULL BACULOVIRUS PSEUDOTYPED WITH THE VESICULAR STOMATITIS VIRUS G PROTEIN THAT IS INFECTIOUS AND PROPAGATES IN Sf9 CELLS". The benefit under 35 USC §119(e) of the United States provisional application is hereby claimed, and the aforementioned application is hereby incorporated herein by reference.

ACKNOWLEDGMENT OF GOVERNMENT SUPPORT

This invention was made with Government support under Grant No. AM33657, awarded by the NIH. The government has certain rights in the invention.

BACKGROUND OF THE INVENTION

1. Field of the Invention

The invention pertains to the field of virology. More particularly, the invention pertains to a genetically engineered baculovirus in which the native envelope protein is absent, and the virus particles are pseudotyped with an envelope protein from another virus.

2. Description of Related Art

Baculoviruses constitute a family of viruses that are pathogenic To certain insect species, but do not appear to productively infect other invertebrates or vertebrates. Baculoviruses, such as the *Autographa californica* Multicapsid Nucleopolyhedrovirus (AcMNPV), have been developed as biological control agents and as protein expression vectors. AcMNPV also serves as the primary model system for studies of baculovirus gene regulation and structure. Baculoviruses have also been used to deliver genes into mammalian cells, and can be used as vectors for human gene therapy.

AcMNPV has a large double stranded DNA genome (134 kbp) and produces two virion phenotypes during the infection cycle. One virion phenotype, the Occlusion Derived Virus or ODV, is adapted for survival in the environment and propagation of infection from animal to animal, through oral transmission and infection of the midgut epithelial cells. In contrast, the other virion phenotype (Budded Virus or BV) is adapted for propagation of infection from cell to cell throughout the animal, after infection is established in the midgut. BV efficiently enter many cell types in the infected animal, including most notably: hemocytes, tracheal epithelial cells, and fatbody cells. The infection cycle is completed when ODV are assembled (enveloped) and occluded within occlusion bodies in the nuclei of these secondarily infected cells. Occlusion bodies are then released by cell lysis.

Because BV are generated only after successful infection of the midgut epithelial cells, BV appear to have adopted a strategy of promiscuous infection of many insect cell types. Studies of baculovirus BV entry into mammalian cell lines and cultured primary cells show that in culture, BV from AcMNPV can efficiently enter primary rat hepatocytes as well as a number of human cell lines, although baculoviruses do not productively replicate there. When a reporter gene driven by a mammalian promoter is inserted into the AcMNPV genome, expression can be readily detected in many mammalian cell types. In contrast, gene expression could not be detected from a reporter under the control of the baculovirus polyhedrin promoter. Thus, baculoviruses appear to efficiently enter mammalian cells and selectively express genes under the control of mammalian promoters. Thus, baculovirus BV can be an effective means for gene delivery to mammalian cells, as gene therapy agents.

Indeed, several features of baculoviruses are highly desirable for the development of baculoviruses as potential vectors for gene therapy. These include the capacity of the baculovirus genome to accommodate very large insertions of foreign DNA, the inability of the virus to replicate within mammalian cells, and the apparent absence of expression of most baculovirus genes. Other studies have shown that baculoviruses incorporating selectable markers (such as the neomycin phosphotransferase II gene) under a mammalian regulatory context, can be used to generate stably transformed mammalian cell lines.

The AcMNPV GP64 protein is an essential virion protein that is involved in both receptor binding and membrane fusion during viral entry. GP64 is also required for viral assembly and efficient production of budded virions (BV) during viral exit.

During virion entry, the AcMNPV GP64 protein is involved in binding of virions to host cells. GP64 also mediates low pH triggered membrane fusion during entry by endocytosis. Genetic studies with gp64-null viruses (containing a gp64 knockout) showed that GP64 is also necessary for efficient virion budding from the cell surface. Interestingly, AcMNPV viruses containing C-terminal truncations of GP64 that removed portions or all of the cytoplasmic tail domain (CTD) did not show the same severity of the defect in budding as the complete GP64 deletion. This indicates that the CTD is not required for efficient budding and that some other feature of GP64 is important for virion assembly and budding. Although the absence of GP64 resulted in an approximately 98% reduction in virion budding, deletion of the CTD resulted in only an approximately 50% reduction in budding efficiency, indicating that other portions of the GP64 protein may play important roles in budding.

GP64 is highly conserved among a number of baculoviruses (such as AcMNPV and OpMNPV) that are relatively closely related, yet several more distantly related baculoviruses possess an unrelated envelope protein that appears to serve as a functional homolog of GP64. The major BV envelope proteins from two of these more distantly related viruses, SeMNPV (Se8) and LdMNPV (Ld130), are both envelope fusion proteins and thus serve at least one of the important functions of GP64. However, these proteins and a homolog from XcGV show a higher degree of divergence than that observed among GP64 proteins. It has therefore been proposed that GP64 may represent a more recent acquisition of an envelope glycoprotein in the Baculoviridae. Several orthomyxoviruses contain an envelope protein, GP75, that is phylogenetically related to the baculovirus GP64 protein. The GP75 proteins have been identified from only a small subset of the orthomyxoviruses and GP75 is distinct from the HA proteins found in other orthomyxoviruses. Therefore, it is possible that the GP75 protein was also recently acquired by a member of the orthomyxovirus family.

In a previous study (Barsoum et al., *Hum Gene Ther.* 8: 2011–8 (1997), the complete disclosure of which is hereby incorporated herein by reference), a baculovirus expressing the VSV-G protein was reported to have an enhanced ability to transduce mammalian cells. In that study, G was expressed in the presence of wt GP64, presumably generating virions with a mosaic of GP64 and G protein in the envelopes. G protein did not appear to interfere with the infectivity of the virus in insect cells but enhanced infectivity of mammalian cells. However, VSV-G protein expression in a baculovirus expression vector in the presence of wt GP64 resulted in a report of virions that were distended and sometimes contained tail-like projections. A potential problem with the utilization of baculovirus virions (BV) containing GP64 for mammalian transduction in vivo, is the rapid detection of GP64 and inactivation of the virus. The use of VSV-G protein or other suitable envelope or membrane proteins substituted for GP64 in the BV envelope could therefore provide benefits for use of baculoviruses in vivo. Retroviruses pseudotyped with VSV-G appear to be more resistant to inactivation by complement than wild type retroviruses, and this may also be true for G-pseudotyped baculovirus particles.

In other enveloped viruses, the role of the major envelope protein in virion budding is highly variable. For example, retroviruses such as HIV-1 or RSV do not require the envelope protein (Env) for virion budding, although virions generated in the absence of Env are not infectious. In contrast, envelope proteins from influenza viruses are believed to encode important functions necessary for virion budding and also influence virion morphology, and these important functions are thought to be redundant in the hemagglutinin (HA) and neuraminidase (NA) proteins of Influenza A virus. Rhabdoviruses such as VSV and Rabies viruses require the major envelope protein (G protein) for efficient budding. In the absence of G, budding of VSV or Rabies virions is reduced by approximately 97%. Heterologous proteins substituted for G can partially complement virion budding in VSV and Rabies rhabdoviruses, and studies suggest that important signals necessary for efficient budding reside in non-specific signals in the cytoplasmic tail domain. Efficient budding of VSV in the absence of intact G protein can be reconstituted by providing only a 'stem' region containing the membrane proximal portion of the G protein ectodomain (12 amino acids) combined with the transmembrane and cytoplasmic tail domains. The small 'stem' region appears to be a functional budding domain necessary to promote efficient budding of VSV in the absence of the majority of the G protein.

One hypothesis to explain the synergistic roles of various proteins in the budding process is the push-pull model, in which the push represents the role of matrix and perhaps other proteins on the inner surface of the plasma membrane, and the pull represents the role of the membrane proteins within and on the exterior of the membrane. Budding may be accomplished by the concerted or synergistic effects of the two components. While a very low level of budding may be observed in the absence of one component, efficient budding would require the activities of both components.

In certain retrovirus and rhabdovirus systems, heterologous envelope proteins can complement the absence of the endogenous envelope protein. Virions carrying a heterologous envelope protein are referred to as 'pseudotyped' viruses. Pseudotyped virions have been used for applications such as gene therapy, but also serve as valuable tools for dissecting the functions necessary for assembly of mature virions and budding at the cell surface. Thus, to better understand the requirements for baculovirus budding, we investigated whether heterologous viral glycoproteins can complement the deletion of the gp64 gene from the AcMNPV genome.

SUMMARY OF THE INVENTION

We investigated whether a heterologous viral envelope protein, the Vesicular Stomatitis Virus (VSV) G protein, can complement the deletion of GP64 in a gp64-null baculovirus, vAc$^{64-}$. To address this question, we generated a stably transfected insect Sf9 cell line (Sf9$^{VSV-G}$) that inducibly expresses the VSV-G protein upon infection with AcMNPV. Sf9$^{VSV-G}$ and Sf9 cells were infected with vAc$^{64-}$ and cells were monitored for infection and for movement of infection from cell to cell. vAc$^{64-}$ formed plaques on Sf9$^{VSV-G}$ cells, but not on Sf9 cells. Plaques formed on Sf9$^{VSV-G}$ cells were observed only after prolonged intervals. Passage and amplification of vAc$^{64-}$ on Sf9$^{VSV-G}$ cells resulted in pseudotyped virus particles that contained the VSV-G-protein. Cell-to-cell propagation of vAc$^{64-}$ in the G-expressing cells is delayed in comparison to wt AcMNPV, and growth curves showed that pseudotyped vAc$^{64-}$ are generated at titres of approximately $10^6$ to $10^7$ infectious units (IU)/ml, compared with titres of approximately $10^8$ IU/ml for wt AcMNPV in the same cells.

Propagation and amplification of pseudotyped vAc$^{64-}$ virions in Sf9$^{VSV-G}$ cells indicates that the VSV-G-protein possesses the necessary signals for baculovirus BV assembly and budding at the cell surface, or otherwise facilitates production of infectious baculovirus virions. The functional complementation of gp64-null viruses by VSV-G protein is further demonstrated by identification of a vAc$^{64-}$-derived virus that acquired the G gene through recombination with Sf9$^{VSV-G}$ cellular DNA. Gp64-null viruses expressing the VSV-G gene are capable of productive infection, replication, and propagation in Sf9 cells. We thus demonstrate herein that several functions of GP64 can be substituted by the VSV-G protein, and we provide the first example of functionally pseudotyped baculovirus virions. We further demonstrate that the VSV-G and two other heterologous envelope protein genes (i.e., two different F proteins from baculovirus Group 2 NPVs) can be engineered into the gp64-null virus genome and functionally complement the absence of GP64. Our results are consistent with a push-pull model for baculovirus budding.

The present invention shows that by expressing VSV-G or another heterologous envelope protein (whether from a cell line, or from the virus), the virus is able to propagate and to infect insect cells. Thus, the VSV-G protein and other heterologous envelope proteins can be inserted into baculovirus virions that contain no GP64 (i.e., a gp64-null baculovirus). We propose that this system is useful for generating baculoviruses targeted to specific cell types (depending on the type of protein or other molecule used to replace GP64). Also, GP64 is a target of immune recognition by the mammalian host (in vivo), and removing GP64 allows the engineered viruses to escape immune surveillance and subsequent inactivation. Immune recognition of GP64 has been demonstrated with recombinant baculoviruses in vivo (injected into mice).

In addition, gp64-null viruses can be used to great advantage in protein expression systems. A foreign gene for expression can be cloned into the GP64-null virus and the virus propagated in a complementing cell line. When the virus is used to infect normal host cells, the foreign protein is expressed, but no virus particles are budded into the culture medium. Thus, purification of expressed foreign proteins is facilitated, as contaminating virus particles do not need to be removed.

We expressed VSV-G (and two other heterologous viral envelope proteins) in the absence of GP64 and found that VSV-G complements virion infectivity and possibly virion budding, although the efficiency of infectious virion production appears to be relatively low. This represents the first example of pseudotyping of baculovirus virions in the absence of the baculovirus GP64 protein. We propose that such pseudotyped baculovirus virions are useful in potential gene therapy applications.

DETAILED DESCRIPTION OF THE INVENTION

In a previous study, it was shown that when the vesicular stomatitis (VSV) G-protein was expressed from a recombinant AcMNPV baculovirus, the presence of G-protein in BV appeared to enhance infectivity in mammalian cells. In that study, BV presumably contained both VSV-G protein and GP64. In the current study, we investigated whether VSV-G protein alone was capable of complementing both virion budding and infectivity in the context of a gp64-null virus, vAc$^{64-}$. To examine this question, we first generated and characterized a Sf9-derived cell line that inducibly expresses the VSV-G protein upon infection with AcMNPV. The cell line, Sf9$^{VSV-G}$, was then infected with vAc$^{64-}$ and cells were monitored for movement of infection from cell to cell. Using this procedure, we generated pseudotyped virions that contain the VSV-G protein and were able to propagate infection from cell to cell in G-expressing cells, but not in Sf9 cells that do not express VSV-G. Although cell-to-cell propagation of the gp64-null virus was delayed in comparison to wt AcMNPV propagation in the G-expressing cells, growth curves showed that pseudotyped virions were generated at titres of approximately $10^6$ to $10^7$ IU/ml, compared with titres of approximately $10^8$ for wt AcMNPV in the same cells.

We demonstrate that the G protein can complement a deletion of GP64. Expression of G from a cell line is sufficient to complement the production of infectious virus particles that could be passaged in G-expressing cells. Although the levels of virions generated are substantially lower than from wt AcMNPV, the success of complementation is underscored by the observation that homologous recombination between the null virus (vAc$^{64-}$) and the Sf9$^{VSV-G}$ cells results in viruses that express the VSV-G protein and are able to propagate infection in Sf9 cells. We have also confirmed this result by directly cloning the VSV-G protein gene into the polyhedrin locus of a gp64-null AcMNPV virus. Similar results were obtained.

Construction of Plasmid pSM8141-VSV-G

Figure 1:
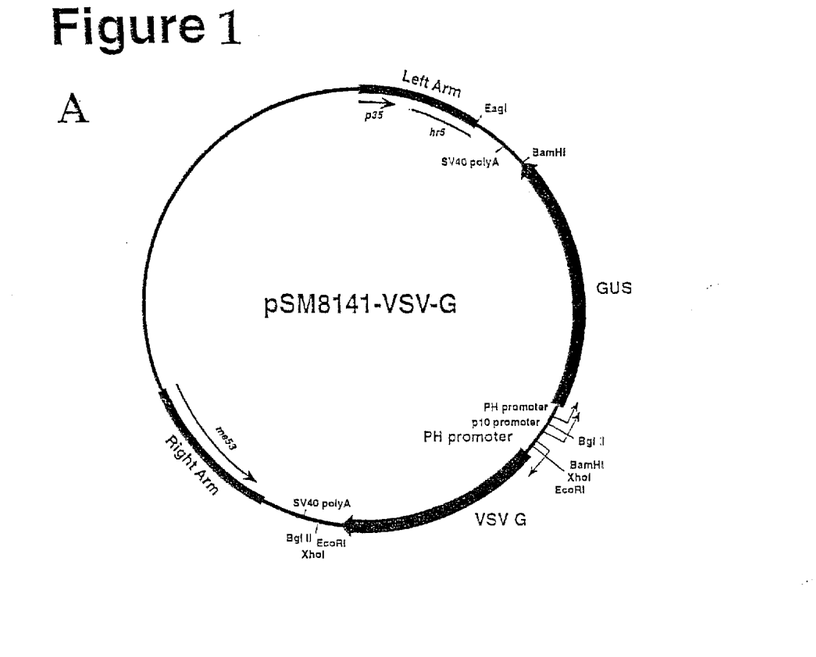
FIG. 1 shows a graphic map of the plasmid pSM8141-VSV-G.
Figure 2:
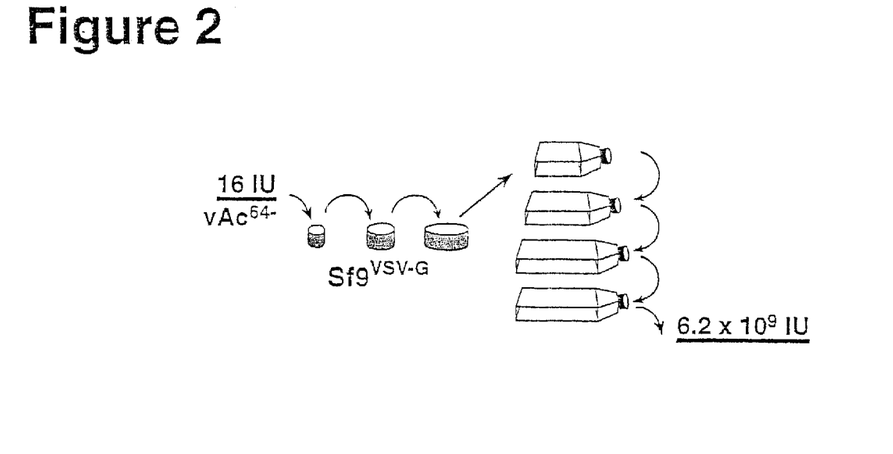
FIG. 2 depicts the procedure used for vAc$^{64-}$ amplification in Sf9$^{VSV-G}$ cells.

Referring to FIG. 1, a graphic map of the plasmid pSM8141-VSV-G is shown. Plasmid pSM8141-VSV-G contains a VSV-G gene under the control of an AcMNPV polyhedrin (PH) promoter and a B-glucuronidase (GUS) gene under the control of both PH and p10 promoters from AcMNPV. Each gene cassette is terminated by an SV40 polyA cleavage and addition site. The two genes are flanked by Left and Right Arm sequences from the AcMNPV p35/hr5 region and the me53 region, respectively. To construct the plasmid, the Vesicular Stomatitis Virus G gene, derived from the Indiana serotype of VSV, was isolated from plasmid VSVG-BP95NOTSV as a 1692 bp Bam HI fragment containing the entire VSV-G open reading frame. The VSV G-protein gene sequence is found under Genbank accession no. NC 001560, which contains the entire VSV genome sequence; the G-protein gene sequence is found at nucleotides 3049–4713. The VSV-G coding gene was inserted into the unique Bam HI site of a dual expression p10 locus transfer plasmid, between a polyhedrin promoter and an SV40 terminator, to create plasmid pSM8135. The presence and orientation of the VSV-G gene was confirmed by sequencing using primers located in the polyhedrin promoter. As a marker for expression in infected insect cells, a Bgl II-Bam HI fragment containing a polyhedrin promoter and Beta-glucuronidase (GUS) reporter gene was inserted into the Bgl II site of plasmid pSM8135 to create plasmid pSM8141-VSV-G.

Generation of Cell Line Sf9$^{VSV-G}$ and Propagation of vAc$^{64-}$ in Sf9$^{VSV-G}$ Cells To generate cells expressing VSV-G protein, Sf9 cells adapted to serum free medium (ESF921) were plated in T75 flasks ($7.5 \times 10^6$ cells per flask) and flasks were transfected with 2 µg pSM8141 plus 1 µg pIE-neo, 2 µg pSM8141 alone, or mock transfected (no DNA added). After transfection, cells were incubated in ESF921 medium for 24 hours, and then resuspended, diluted 1:4 and replated in T75 flasks. ESF921 medium was replaced with ESF921 containing 1 mg/ml G418. After two weeks, cells were monitored to confirm that all mock transfected cells were dead. Small cell colonies that grew only from the cells transfected with pSM8141 plus pIE-neo were selected as single, well isolated colonies, and were picked using sterile micropipettor tips and transferred to individual wells of a 24 well dish, and cultured in ESF921 plus 5% FBS. A cell line derived from one colony was selected and designated Sf9$^{VSV-G}$.

Cell lines Sf9, Sf9$^{Op1D}$, and Sf9$^{VSV-G}$ were propagated at 27° C. in TNMFH medium containing 10% fetal bovine serum. Sf9$^{Op1D}$ cells were used only at passages under 250. The wild type (wt) AcMNPV virus used was AcMNPV strain E2. Construction of the gp64-null virus, vAc64$^-$, was described previously by Oomens et al. in "Requirement for GP64 to drive efficient budding of Autographa californica Multicapsid Nucleopolyhedrovirus," Virology 254: 297–314 (1999), the complete disclosure of which is hereby incorporated herein by reference. Infectious vAc64$^-$ was generated in Sf9$^{Op1D}$ cells by infecting cells at a multiplicity of infection (MOI) of 1, followed by harvest of virus at approximately 3 days post infection. vAc64$^-$ was titred on Sf9$^{Op1D}$ cells. Virus stocks of vAc64$^-$ were monitored for the presence of rescued virus containing the OpMNPV gp64 gene by infecting Sf9 cells at low MOI (approximately $1 \times 10^{-2}$ to $1 \times 10^{-4}$), followed by prolonged incubation and observation for infected cells capable of propagating infection.

To determine if the presence of VSV-G protein is sufficient to facilitate the production of infectious baculovirus in the absence of GP64, a gp64-null virus (vAc$^{64-}$) containing no gp64 gene was used to infect Sf9$^{VSV-G}$ cells. Infected cells were examined for the capacity to propagate the gp64-null virus infection. Three cell lines were infected with virus vAc$^{64-}$: Sf9$^{Op1D}$, a Sf9 derived line expressing the OpMNPV GP64 protein, that was previously shown to complement vAc$^{64-}$(28, 30); Sf9, a line that does not support propagation of vAc$^{64-}$; and Sf9$^{VSV-G}$, a line that inducibly expresses VSV-G protein. The gp64-null virus used for these experiments was propagated in Sf9$^{Op1D}$ cells as described previously in Virology 254: 297–314 (1999), the complete disclosure of which is hereby incorporated herein by reference. The virus inoculum contained the OpMNPV GP64 protein in the envelope, but no gp64 gene in the viral genome.

Each cell line was infected with vAc$^{64-}$ and plaque formation was examined over an extended time period. As expected, vAc$^{64-}$ infection of Sf9$^{Op1D}$ cells resulted in abundant formation of plaques as OpMNPV GP64 is known to complement the AcMNPV gp64 deletion. In contrast, vAc$^{64-}$ infection of Sf9 cells resulted in an initial infection of single cells, but the virus failed to propagate from cell to cell and did not form plaques. In vAc$^{64-}$ infected Sf9$^{VSV-G}$ cells, we initially observed single infected cells and plaques were not clearly visible at 5–7 days p.i. However, upon further incubation, plaques were detected in Sf9$^{VSV-G}$ cells by 10 days p.i., and had expanded significantly by 16–18 days p.i. These observations indicate that the VSV-G protein is capable of complementing the defect in the gp64 null virus, vAc$^{64-}$, although virus propagation appears to be delayed. The formation of plaques indicates that the defects in both virion entry and exit are complemented.

To further examine this question, and to confirm that the null virus can be propagated and amplified in Sf9$^{VSV-G}$ cells, we performed the following experiment. Sf9, Sf9$^{Op1D}$, or Sf9$^{VSV-G}$ cells were infected with vAc$^{64-}$ at an MOI of $2.2\times10^{-5}$ (1 IU per $4.5\times10^4$ cells) and cells were incubated at 27° C. until they were 90% confluent. The medium and cells from each well were then transferred into successively larger wells and then to T-flasks. At each step, cells were transferred when they reached approximately 90% confluency. Passage of vAc$^{64-}$ in Sf9$^{Op1D}$ cells in this manner resulted in a rapid propagation of infection, such that cell growth was arrested and all cells were infected after the third passage. This was expected, since the GP64 protein expressed by the Sf9$^{Op1D}$ cells complements the absence of GP64 in virus vAc$^{64-}$. Attempted passage of vAc$^{T-}$ in Sf9 cells in this manner resulted in no spread of infection. Although vAc$^{64-}$ appeared to propagate slowly in Sf9$^{VSV-G}$ cells, continued passage resulted in increasing numbers of infected cells until most cells were infected at passage six or seven. Supernatants were then harvested and viruses were titred on Sf$_9$$^{Op1D}$ cells, which are sensitive indicators of infection by the gp64-null virus. We measured $6.2\times10^9$ IU from the vAc$^{64-}$ virus passaged in Sf9$^{VSV-G}$ cells in the manner described above. Thus the vAc$^{64-}$ virus was amplified approximately $3.9\times10^8$ fold in Sf9$^{VSV-G}$ cells in this experiment. Herein we refer to the vAc$^{64-}$ that was amplified in Sf9$^{VSV-G}$ cells as pseudotyped virus or $^G$vAc$^{64-}$.

Expression of VSV-G in Sf9$^{VSV-G}$ Cells

Because it was previously reported that expression of VSV-G is toxic in some cell lines, we used a strategy in which expression of VSV-G in insect Sf9 cells was dependent on infection with AcMNPV. The plasmid pSM8141-VSV-G, containing the VSV-G gene under the control of an AcMNPV polyhedrin promoter (FIG. 1), was constructed and cotransfected into Sf9 cells with the plasmid pIE1-neo, which contains the *E. coli* neomycin phosphotransferase II gene under the control of the AcMNPV IE1 promoter. G418 was used to select and clone a cell line that was designated Sf9$^{VSV-G}$. To determine whether the VSV-G gene was inserted into the cell line, and whether expression of VSV-G was inducible by infection with AcMNPV, we examined induced (infected) and uninduced (mock-infected) Sf9$^{VSV-G}$ cells by western blot analysis and immunofluorescence microscopy, and compared VSV-G expression in mock-infected and infected Sf9$^{VSV-G}$ cells.

VSV-G protein was detected in Sf9$^{VSV-G}$ cells infected with either wt AcMNPV or vAc$^{64-}$, but was not detected in mock-infected cells. An antiserum directed against the major capsid protein (VP39) was used as an internal control to confirm infection. Detection of VSV-G by immunofluorescence microscopy showed that VSV-G was detected from AcMNPV or vAc64$^-$ infected Sf9 cells, but not from mock-infected Sf9$^{VSV-G}$ cells or Sf9 cells infected with wt AcMNPV. Immunofluorescent staining of infected cells was consistent with VSV-G presence at the periphery of infected cells, indicating that G was likely transported to the surface of these cells. Thus, infection of cell line Sf9$^{VSV-G}$ with wt AcMNPV or vAc$^{64-}$ results in the induction of VSV-G protein expression and G appears to be appropriately localized within these cells.

SDS-PAGE and Western Blot Analysis

For western blot analysis of GP64, VSV-G, and VP39 proteins, cells were infected at an MOI of 1 and harvested at 46–75 hours post-infection (p.i.), then examined for VSV-G protein expression and VP39 protein expression, using monoclonal antibodies (anti-GP64 MAb AcV5, anti-VSV-G MAb P5D4, or anti-VP39 MAb P10). Samples were prepared for western blot analysis in the following manner. Cell extracts from infected or uninfected cells were lysed in 1× Laemmli buffer (125 mM Tris, 2% SDS, 5% 2-mercaptoethanol, 10% glycerol, 0.001% bromophenol blue, pH 6.8) and heated to 100° C. for 5 minutes prior to storage at −20° C. or electrophoresis. Virions of wt AcMNPV or pseudotyped $^G$vAc64$^-$ BV were prepared from tissue culture supernatant by centrifugation at 80,000× g for 75 minutes at 4° C. through a 25% sucrose cushion in PBS, and subsequent resuspension of the pellet in 1× Laemmli buffer. Samples were heated to 100° C. for 5 minutes and electrophoresed through 10% SDS-PAGE gels. Approximately $2.6\times10^4$ cells or $8\times10^6$ virions were electrophoresed in each lane. Gels were blotted onto Immobilon-P filters and incubated with the following primary monoclonal antibodies: AcV5, an anti-GP64 MAb; MAb P10, an anti-VP39 MAb; or P5D4, an anti VSV-G MAb. Monoclonal antibodies were diluted 1:100, 1:1,000, and 1:100,000, respectively in TBST (10 mM Tris pH 8, 150 mM NaCl, 0.05% Tween 20) with 0.02% sodium azide. After washing, blots were incubated with a secondary antibody consisting of a goat-anti-mouse IgG-alkaline phosphatase conjugate at a dilution of 1:10, 000. Western blots were then processed as described previously by Blissard, et al. in "Baculovirus GP64 envelope glycoprotein is sufficient to mediate pH dependent membrane fusion," J. Virol. 66: 6829–6835 (1992), the complete disclosure of which is hereby incorporated herein by reference.

To confirm that the amplified virus ($^G$vAc$^{64-}$) did not result from contamination with wt AcMNPV or a gp64-null virus that acquired the OpMNPV gp64 gene during prior propagation in Sf9$^{Op1D}$ cells, we used western blot analysis to examine cells infected with either wt AcMNPV, vAc$^{64-}$, or $^G$vAc$^{64-}$. The GP64 protein was detected from cells infected with wt AcMNPV and from virus infections in Sf9$^{Op1D}$ cells, which constitutively expresses OpMNPV GP64. In addition, a weak GP64 signal was frequently observed from cells infected with vAc$^{64-}$. Because vAc$^{64-}$ was previously passaged in Sf9$^{Op1D}$ cells and carries wt OpMNPV GP64 in the envelope, low levels of GP64 detected from these samples can result from GP64 carried in with the inoculum virus. However, the GP64 protein was not detected from Sf9 or Sf9$^{VSV-G}$ cells infected with $^G$vAc$^{64-}$. VSV-G was detected in all infected Sf9$^{VSV-G}$ cells, as expected.

Interestingly, a strong VSV-G signal was detected in extracts from all cells infected with the pseudotyped virus, $^{G}vAc^{64-}$. A plausible explanation for this result was that some of the $^{G}vAc^{64-}$ virus may have acquired the VSV-G gene during passage through the Sf9$^{VSV-G}$ cells and thus was expressing G protein from the virus genome. This possibility was addressed in detail in subsequent experiments. In the current experiments, we found that GP64 was not detected in Sf9 or Sf9$^{VSV-G}$ cells infected with the G-pseudotyped virus (i.e., $^{G}vAc^{64-}$). Thus, the observed propagation of vAc$^{64-}$ in Sf9$^{VSV-G}$ cells was not due to contamination with a virus expressing GP64. In addition, these data confirm that the gp64-null virus (vAc$^{64-}$) can be propagated in G-expressing cells, in the absence of GP64.

Immunofluorescence Microscopy

For immunofluorescent detection of VSV-G protein in Sf9 or Sf9$^{VSV-G}$ cells infected with wt AcMNV or vAc$^{64-}$, cells were infected with the indicated viruses at an MOI of 10, then fixed at 40 hours p.i. and immunostained with MAb P5D4 and goat-anti-mouse FITC. Cells were examined and photographed by epifluorescence microscopy. For immunofluorescence staining, 1×10$^5$ Sf9 or Sf9$^{VSV-G}$ cells were plated per well on 2-well slides and cells were allowed to attach for 1 hour, then mock-infected or infected with AcMNPV or vAc$^{64-}$ (MOI 10) for 1 hour. At 40 hours p.i., cells were washed 3 times with 1 ml PBS (pH 6.4) per well, then fixed in 100% methanol at −20° C. for 10 min. Cells were then air-dried 10 minutes and rehydrated in 300 µl buffer A (5% filtered FBS, 0.1% saponin, 1× PBS) for 10 min. Cells were then incubated with anti-VSV-G antibody (P5D4, mouse ascites fluid, Sigma), diluted 1:10,000 in buffer A (described above) for 45 minutes at room temperature (RT). After 3 washes with 300 µl Buffer A (10 min/wash), cells were incubated with a 1:100 dilution of goat anti-mouse IgG FITC conjugate for 30 minutes at RT. Cells were washed 4× with buffer A, then sealed in GelMount and viewed on an Olympus IX70 epifluorescence microscope.

Plaque Assays, Growth Curves and TCID$_{50}$ Assays

Plaque assays were performed in six well plates, as previously described in J. Virol. 66: 6829–6835 (1992), the complete disclosure of which is hereby incorporated herein by reference. Sf9, Sf9$^{Op1D}$ and Sf9$^{VSV-G}$ cells were plated at 1.5×10$^6$ cells/well, and after a 1 hour attachment period, a monolayer of cells (Sf9$^{Op1D}$, Sf9$^{VSV-G}$, or Sf9) was infected with vAc$^{64-}$ at several dilutions. Cells were monitored for infection and plaque formation over an 18 day period, and at 10 or 18 days, each well was overlaid with 50 µg/ml neutral red in 1% agar and infected cells were examined at the indicated intervals (5, 7, 10, 14, or 16 days). Infected cells containing occlusion bodies appear as dark cells against the background of lighter cells. Plaque formation and morphology in vAc$^{64-}$ infected Sf9$^{Op1D}$, Sf9$^{VSV-G}$, and Sf9 cell monolayers were examined after 10 and 18 days, respectively. Growth curves were carried out by a modification of the protocol described in Virology 254: 297–314, the complete disclosure of which is hereby incorporated herein by reference. Sf9 cells were infected with AcMNPV, and Sf9$^{Op1D}$ and Sf9$^{VSV-G}$ cells were infected with vAc64$^-$ at an MOI of 5. After an initial 1 hour infection period, cells were washed 3× with TNMFH and supernatants were collected at the indicated time points. Data from each time point represents accumulated infectivity from infection through the indicated time. All supernatants were titred by TCID$_{50}$ assay on Sf9$^{Op1D}$ cells.

In our initial analysis of vAc$^{64-}$ virus propagation in Sf9$^{VSV-G}$ cells, we observed that plaque formation was significantly delayed, when compared with plaque formation by the same virus in Sf9$^{Op1D}$ cells. This could result from a delay in the infection cycle, low virus yield, lowered infectivity of the pseudotyped virus, or some combination of these factors. To examine the kinetics of virion production in vAc$^{64-}$ infected Sf9$^{VSV-G}$ cells, we generated a one step growth curve of infectious virus production, and compared that curve to similar curves generated from wt AcMNPV infected Sf9 cells, and vAc$^{64-}$ infected Sf9$^{Op1D}$ cells. Because the infectivity of virions carrying VSV-G protein may differ from those carrying GP64, and because the observed propagation of viruses in G-expressing cells was delayed, all virus samples collected from growth curve experiments were titred on Sf9$^{Op1D}$ cells.

Figure 3:
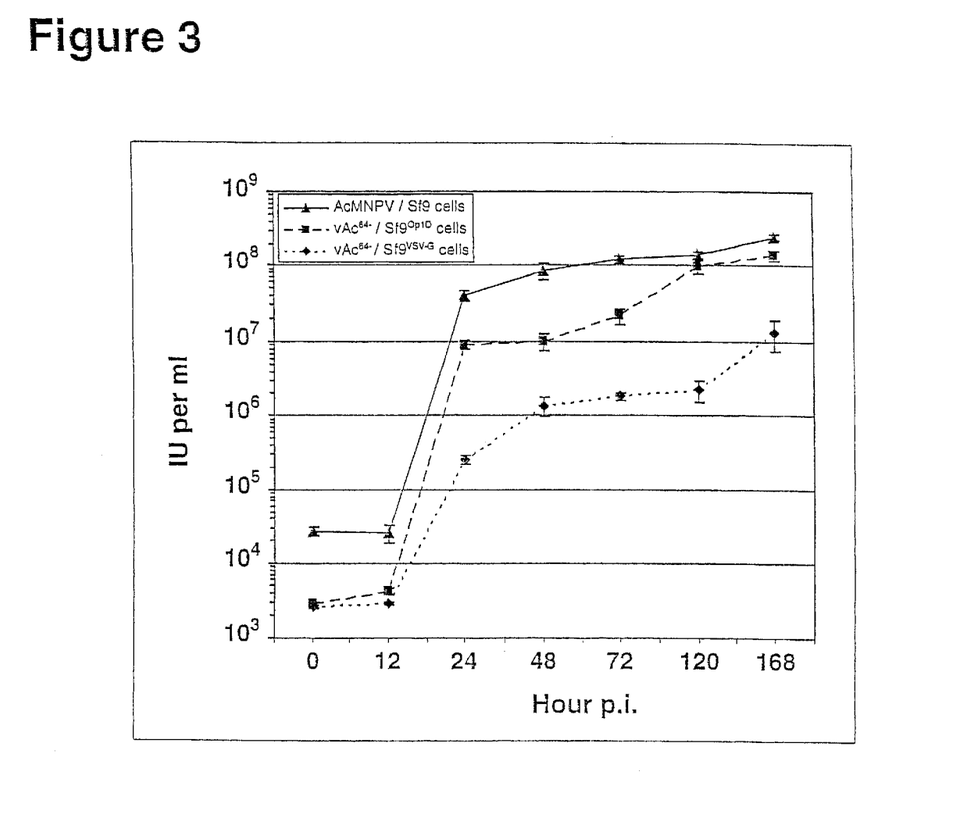
FIG. 3 shows data from one step growth curves.

FIG. 3 shows growth curve data for the gp64-null virus (i.e., vAc64$^-$) in cells expressing VSV-G (Sf9$^{VSV-G}$) or OpMNPV GP64 (Sf9$^{Op1D}$). For comparison, a growth curve of wt AcMNPV infected Sf9 cells is also plotted. Cells were infected and supernatants collected at the indicated times post infection, and virus yields were determined by titration on Sf9$^{Op1D}$ cells. Each virus-cell combination is indicated in the inset. Each data point represents 3 individual infections, and error bars are indicated. Each cell line (Sf9, Sf9$^{VSV-G}$ or Sf9$^{Op1D}$) was infected at an MOI of 5 with either wt AcMNPV or vAc$^{64-}$, and supernatants were harvested at the indicated times post infection. Supernatants were then titred on Sf9$^{Op1D}$ cells. The temporal kinetics of the growth curves of all viruses were similar (FIG. 3), although peak virion production of the G pseudotyped vAc$^{64}$ appeared to lag behind that of wt AcMNPV infected Sf9 cells and vAc$^{64-}$ infected Sf9$^{Op1D}$ cells. For the two control infections (AcMNPV in Sf9 cells or vAc$^{64-}$ in Sf9$^{Op1D}$ cells), titres of 1×10$^7$ IU/ml were observed by 24–48 hours p.i. In contrast, vAc$^{64-}$ infected Sf9$^{VSV-G}$ cells produced titres in the range of 10$^5$ IU/ml at 24 hours and approximately 10$^6$ IU/ml by 48 hours. Titres of the pseudotyped virus gradually increased to 10$^7$ IU/ml at 168 hours p.i. AcMNPV infected Sf9 cells and vAc$^{64-}$ infected Sf9$^{Op1D}$ cells generated titres of approximately 10$^8$ IU/ml by 72–120 hours p.i. Thus, while the kinetics of virus production were generally similar, the production of virus particles that were pseudotyped with VSV-G protein lagged slightly behind that of wt AcMNPV, and final yields of infectious virus were reduced by at least one log and represented approximately 10% of the final yield from wt AcMNPV.

PCR Analysis

For preliminary PCR analysis, oligonucleotide primers specific to regions within the VSV-G, gp64, p35, or vp39 open reading frames were designed. Primer pairs were composed of oligonucleotides with the following nucleotide sequences:

Primer pair VSV-G=5'-tccgatccttcactccatctg-3' (SEQ ID NO: 1) and 5'-tagctgagatccactggagag-3' (SEQ ID NO: 2);

Primer pair gp64=5'-gttgttattggctacaagggc-3' (SEQ ID NO: 3) and 5'-tgagtagagcgtggcgttgagc-3' (SEQ ID NO: 4);

Primer pair p35=5'-cagaattcatgtgtgtaattttccggtag-3' (SEQ ID NO: 5) and 5'-aatgctctagattatttaattgtgtttaatattac-3' (SEQ ID NO: 6);

Primer pair vp39=5'-cgggatccaatggcgctagtgcccgtgggtatgg-3' (SEQ ID NO: 7) and 5'-cgggatccgcgacggctattcctccacctgcttc-3' (SEQ ID NO: 8).

PCR amplification reactions contained 0.3 µM of each primer in a pair, 0.3 mM dATP, dCTP, dGTP, dTTP, 50 mM KCl, 10 mM Tris-HCL pH 8.3, 1.5 mM MgCl 0.1% Triton X100, and 0.4 U Taq DNA Polymerase in a final volume of 20 µl. Reactions were subjected to 94° C. for 3 minutes, followed by 3 cycles at an annealing temperature of 52° C., then 27 cycles at an annealing temperature of 53° C., where each cycle consists of denaturation at 94° C. for 30 seconds, annealing at the prescribed temperature (above) for 40 seconds, and extension at 72° C. for 1.5 minutes. The final extension was held at 72° C. for 10 minutes. Products were electrophoresed on 1% agarose gels and stained with ethidium bromide.

Figure 4:
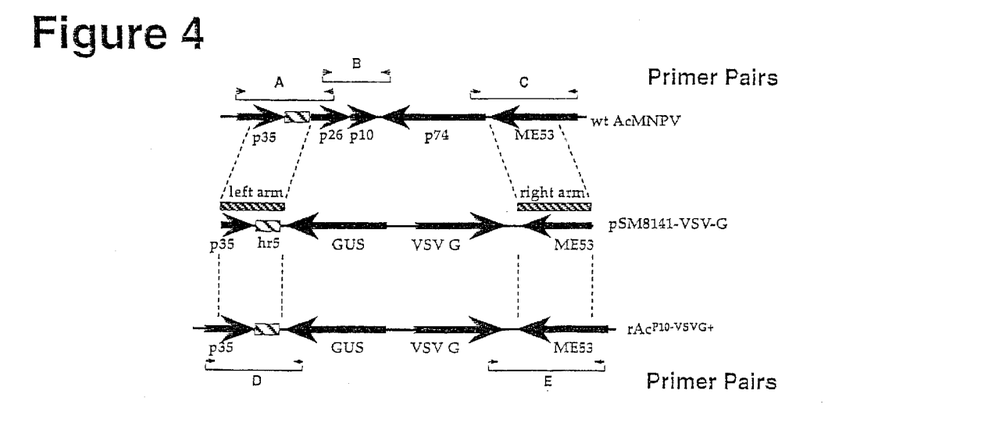
FIG. 4 shows a graphic map of the primer pairs used in PCR analysis of the p10 locus of AcMNPV in wt, vAc$^{64-}$, and Sf9$^{VSV-G}$ virus isolates.

To amplify portions of the p10 locus from the genomes of wt and pseudotyped viruses, we used primer pairs that would amplify: a) fragments from only the intact p10 locus (FIG. 4, primer pairs A, B, and C) or b) portions of the VSV-G and p10 locus if the VSV-G gene were integrated at the predicted site (FIG. 4, primer pairs D and E). Each 50 $\mu$l reaction contained 0.3 $\mu$M of each primer, 0.3 mM dATP, dCTP, dGTP, dTTP, 10 mM KCl, 10 mM $(NH_4)_2SO_4$, 20 mM Tris-HCl pH 8.8, 2 mM $MgSO_4$, 0.1% Triton X100, and 0.6 U Vent DNA polymerase. Amplification reactions were held at 94° C. for 3 minutes, followed by 30 cycles of 94° C. for 45 seconds, 53° C. for 45 seconds, and 72° C. for 5 minutes. Finally, reactions were held at 72° C. for 5 minutes. Primer pairs consisted of oligonucleotides with the following nucleotide sequences:

Primer pair A=5'-tgcgtgttgaagccgggatttg-3' (SEQ ID NO: 9) and 5'-gtcccgacagctgggacgcct-3' (SEQ ID NO: 10);
Primer pair B=5'-cgaatggctgttaccggtgacg-3' (SEQ ID NO: 11) and 5'-ctcgctatacactcgcatggag-3' (SEQ ID NO: 12);
Primer pair C=5'-cgatgcatatgtatggcatacc-3' (SEQ ID NO: 13) and 5'-gagtttgggaacaagtttgaagg-3' (SEQ ID NO: 14);
Primer pair D=5'-tgcgtgttgaagccgggatttg-3' (SEQ ID NO: 15) and 5'-gtgaagagtatcagtgtgcatg-3 (SEQ ID NO: 16)';
Primer pair E=5'-gtagaaggttggttcagtagttg-3' (SEQ ID NO: 17) and 5'-gagtttgggaacaagtttgaagg-3' (SEQ ID NO: 18).

Referring now to FIG. 4, a graphic map of the primer pairs used in PCR analysis of the p10 locus of AcMNPV in wt. $vAc^{64-}$, and $Sf9^{VSV-G}$ virus isolates is shown. For PCR analysis of viral DNAs from cell lysates of Sf9 cells infected with $^GvAc^{64-}$ gene, several specific primer pairs (not shown) were used to examine isolates for the presence of the OpMNPV gp64 gene or the VSV-G gene. The arrows in FIG. 4 show the locations of the primers on the wt AcMNPV and $vAc^{64-}$ genomes, and on the putative genome of $^GvAc^{64-}$ isolates, in which VSV-G could have integrated. DNAs from infected Sf9 cell lysates were used as templates for PCR analysis of p10 locus in $vAc^{64-}$ (primer pairs A, B, and C), or the putative p10 locus in which VSV-G is predicted to integrate into the $^GvAc^{64-}$ genome (primer pairs D, and E). The sequences of the gene-specific primer pairs are indicated above.

Electron Microscopy

For transmission electron microscopy, virions were purified from cell culture supernatants, then fixed, embedded, sectioned and stained. For each virus preparation (wt AcMNPV or $^GvAc^{64}$), 33 ml of infected cell culture supernatants (representing $1\times10^9$ or $3\times10^9$ IU, respectively) were pelleted by centrifugation at 80,000× g for 75 minutes at 4° C. through a 25% sucrose cushion. The resulting virus pellet was fixed in 2.5% gluteraldehyde in 100 mM cacodylate buffer (pH 7.2), then postfixed in 1.5% osmium tetroxide overnight at 4° C. After fixing, cells were dehydrated through a graded series of EtOH washes and embedded in Spurr's embedding medium. Ultrathin sections were stained by incubation for 5–30 minutes in 2% uranyl acetate in $H_2O$, washed 3× in $dH_2O$, then stained for 5 minutes in Reynolds lead citrate, and washed 5× in $dH_2O$. Sections were examined at magnifications of 15,000× and 70,000× at 80 or 100 kV on a Phillips 201 transmission electron microscope.

To determine if virions generated in the presence of the VSV-G protein, and in the absence of GP64, were altered in morphology, we used transmission electron microscopy to compare $^GvAc^{64-}$ virions with those from wt AcMNPV. An obvious initial difference between preparations of wt AcMNPV and $^GvAc^{64}$, was the presence of numerous vesicles of varying sizes. Such vesicles may result from vesicle budding mediated by expression of the G protein. Vesiculation has been previously reported in mammalian cells expressing VSV-G protein. Infectious virus titres were lower in the $^GvAc^{64-}$ preparation and virus particles were less numerous compared with wt AcMNPV preparations. However, $^GvAc^{64-}$ virions were clearly visible. wt AcMNPV BV consist of enveloped rod-shaped nucleocapsids. The envelope is typically composed of an apparently loosely adhering (lipid bilayer) membrane with a thickened region in the membrane, near one end of the rod-shaped nucleocapsid. These characteristics were also typical of BV from the $^GvAc^{64-}$ preparation. We did not typically observe nucleocapsids within enlarged or distended envelopes and nucleocapsids within larger vesicles were not observed. Thus, although $^GvAc^{64-}$ virions were less abundant, $^GvAc^{64-}$ virions appeared to be similar in morphology to those from wt AcMNPV and they were not morphologically distinguishable.

Examination of virions generated from the G-pseudotyped gp64-null virus used in this study showed clearly that virions were similar in morphology to wt AcMNPV virions. Nucleocapsids were not observed within vesicles or within virions that appeared as oval-shaped particles with tail-like structures as reported earlier.

Biochemical and Genetic Analysis of $^GvAc^{64-}$ BV

Virus particles pseudotyped with VSV-G protein were examined biochemically for the presence of the G protein. $^GvAc^{64-}$ virions were prepared from supernatants of $vAc^{64-}$ infected $Sf9^{VSV-G}$ cells after multiple passages in $Sf9^{VSV-G}$ cells, then examined by Western blot analysis. As a comparison, wt AcMNPV virions were examined in parallel. Preparations of $^GvAc^{64-}$ virions contained substantial quantities of G, but GP64 was not detected. In wt AcMNPV preparations produced in Sf9 cells, G protein was not detected. Detection of the major capsid protein, VP39, was similar in both wt AcMNPV, and $^GvAc^{64-}$ preparations.

Because VSV-G was detected at relatively high levels in cells infected with $^GvAc^{64-}$, and VSV-G was also abundant in virion preparations, it was possible that the VSV-G gene was acquired by the $vAc^{64}$- virus through homologous recombination. We therefore investigated whether the VSV-G gene could be identified in DNA from $^GvAc^{64-}$ virions prepared after passage in $Sf9^{VSV-G}$ cells. DNA prepared from virions of $^GvAc^{64-}$, $vAc^{64-}$ (passaged in $Sf9^{Op1D}$ cells), or OpMNPV were used with a series of oligonucleotide primers to amplify portions of the VSV-G ORF, the OpMNPV gp64 ORF, and the AcMNPV p35 and vp39 ORFs. Primers specific for portions of the AcMNPV p35 and vp39 ORFs were included as positive controls for AcMNPV genes, and the OpMNPV gp64 ORF specific primers were included as a control to confirm that viruses did not acquire the gp64 gene during propagation in $Sf9^{Op1D}$ cells. As expected, p35 and vp39-specific primers amplified the expected PCR products (900 and 1044 bp, respectively) from $^GvAc^{64-}$ and $vAc^{64-}$ DNAs but not from OpMNPV DNA. The OpMNPV gp64 specific primers amplified the appropriate (1259 bp) fragment from only the OpMNPV DNA, indicating that the OpMNPV GP64 gene was not present in $^GvAc^{64-}$ and $vAc^{64-}$ DNAs. Using VSV-G specific primers, a 673 bp fragment was amplified from $^GvAc^{64-}$ virion DNA, but not from $vAc^{64-}$ virion DNA. Thus, these data suggest that $^GvAc^{64-}$ virions acquired the VSV-G gene during propagation in the $Sf9^{VSV-G}$ cells.

If the $^G$vAc$^{64-}$ virus acquired the G gene, this virus should no longer require the Sf9$^{VSV-G}$ cells for propagation. To determine whether acquisition of the G gene would permit the $^G$vAc$^{64-}$ virus to propagate independently of the Sf9$^{VSV-G}$ cell line, we infected Sf9 cells with a $^G$vAc$^{64-}$ virus preparation that was passaged in Sf9$^{VSV-G}$ cells. This resulted in a spreading infection and the virus was passaged twice in Sf9 cells (5 days per passage), then several isolates were generated by limiting dilutions in Sf9 cells. G-specific primer pairs were used to examine DNA from infected cell lysates by PCR. We found that the VSV-G gene was present in five virus preparations generated in this manner, indicating that each contained viruses with a copy of the VSV-G gene. Although these viruses were able to propagate in Sf9 cells, each isolate was negative for the OpMNPV gp64 gene, indicating that virus propagation in Sf9 cells was not due to contamination with a virus that acquired the OpMNPV gp64 gene from Sf9$^{Op1D}$ cells.

Because the plasmid used to generate the Sf9$^{VSV-G}$ cell line was derived from a transfer vector plasmid that was originally designed for cloning into the AcMNPV p10 locus, we reasoned that acquisition of VSV-G by the vAc$^{64-}$ virus may occur by homologous recombination at the p10 locus. We therefore used a PCR strategy to examine the p10 locus of viral isolates passaged first in Sf9$^{VSV-G}$ cells, then in Sf9 cells. FIG. 4 shows the PCR strategy. As expected, the appropriate PCR products were identified from the parental virus, vAc$^{64-}$, when primer pairs specific for the wt AcMNPV p10 locus were used. In addition, no PCR products were detected from vAc$^{64-}$ template when primers specific for the predicted VSV-G insertion were used.

Interestingly, DNAs from $^G$vAc$^{64-}$ that was passaged first through the Sf9$^{VSV-G}$ cells, then through Sf9 cells, were positive for both sets of primers. This indicates that genotypes containing a) a wt p10 locus and b) a VSV-G insertion in the p10 locus, were both present in the preparation. Other similarly derived isolates also showed the same result, indicating that these virus preparations likely contained mixtures of parental viruses (vAc$^{64-}$) and recombinant viruses in which the G gene was inserted at the p10 locus. We propose that, because these recombinant viruses abundantly express G protein, they may serve as helper viruses for the defective vAc$^{64-}$ viruses containing no GP64 envelope protein.

In summary, we found that the VSV-G protein was sufficient to complement the defect in the vAc$^{64-}$ (gp64-null) virus when G was provided by the cell line Sf9$^{VSV-G}$. In addition this complementation appears to result in sufficient selection pressure so that the G gene becomes integrated into the genome of vAc$^{64-}$. We detected integration of the VSV-G gene in the p10 locus of vAc$^{64-}$ in several viral isolates, and found that these viruses were capable of independent propagation in SF9 cells.

We expressed VSV-G in the absence of GP64 and found that VSV-G complements virion infectivity and possibly virion budding, although the efficiency of infectious virion production appears to be relatively low. This represents the first example of pseudotyping of baculovirus virions in the absence of the baculovirus GP64 protein. We propose that such pseudotyped baculovirus virions are useful in potential gene therapy applications.

Baculoviruses are subdivided into two groups. While the budded virions from one group (Group 1 NPVs) contain the GP64 protein, those from other groups (Group 2 NPVs and GVs) contain an unrelated protein (F-protein) that serves a similar functional role. We have demonstrated that at least 2 of the F-proteins from Group 2 NPVs also complement infectivity in the context of a gp64-null genotype.

Envelope proteins from Rhabdoviridae other than VSV (such as, for example, rabies virus) also are expected to complement infectivity of the gp64-null baculovirus, as described herein, as are envelope proteins from other families of viruses, such as, for example, Orthomyxoviridae, Paramyxoviridae, Filoviridae, Retroviridae, as well as herpesviruses, poxviruses and hepadnaviruses.

Finally, chimeric envelope proteins that consist of parts of GP64 and parts of other envelope proteins, or parts of two or more different envelope proteins, also are expected to complement infectivity of the gp64-null baculovirus, as described here.

Accordingly, it is to be understood that the embodiments of the invention herein described are merely illustrative of the application of the principles of the invention. Reference herein to details of the illustrated embodiments is not intended to limit the scope of the claims, which themselves recite those features regarded as essential to the invention.

What is claimed is:

1. A genetically engineered baculovirus, comprising:
a deletion, inactivation or downregulation of an envelope protein gene of a progenitor baculovirus, from which said engineered baculovirus is derived, wherein said genetically engineered virus is supplied, in trans or cis, with a heterologous envelope protein or a protein or other molecule that facilitates entry of said engineered baculovirus into a cell that is not normally a host of said progenitor baculovirus, wherein said heterologous protein or other molecule is riot derived from a baculovirus.

2. The genetically engineered baculovirus of claim 1, having a property of more efficient entry into a non-host cell than said progenitor baculovirus, from which said engineered baculovirus is derived.

3. The genetically engineered baculovirus of claim 1, having a property of more specific targeting of said engineered baculovirus to a specific cell type than said progenitor baculovirus, from which said engineered baculovirus is derived.

4. The genetically engineered baculovirus of claim 1, having a property of more effective evasion of mammalian immune system recognition or inactivation than said progenitor baculovirus, from which said engineered baculovirus is derived.

5. A genetically engineered baculovirus, comprising:
a deletion, inactivation or downregulation of an envelope protein gene of a progenitor baculovirus, from which said engineered baculovirus is derived, wherein said genetically engineered baculovirus is farther engineered to express an envelope protein from another virus, which is not a baculovirus.

6. The genetically engineered baculovirus of claim 5, having a property of more efficient entry into a non-host cell than said progenitor baculovirus, from which said engineered baculovirus is derived.

7. The genetically engineered baculovirus of claim 5, having a property of more specific targeting of said engineered baculovirus to a specific cell type than said progenitor baculovirus, from which said engineered baculovirus is derived.

8. The genetically engineered baculovirus of claim 5, having a property of more effective evasion of mammalian immune system recognition or inactivation than said progenitor baculovirus, from which said engineered baculovirus is derived.

9. The genetically engineered baculovirus of claim 5, wherein said progenitor baculovirus envelope protein is gp64 of a homologous envelope glycoprotein.

10. A genetically engineered baculovirus, comprising:
a deletion, inactivation or downregulation of an envelope protein gene of a progenitor baculovirus, from which said engineered baculovirus is derived, wherein said genetically engineered baculovirus is further engineered to express an envelope protein from Vesicular Stomatitis Virus.

11. The genetically engineered baculovirus of claim 10, having a property of more efficient entry into a non-host cell than said progenitor baculovirus, from which said engineered baculovirus is derived.

12. The genetically engineered baculovirus of claim 10, having a property of more specific targeting of said engineered baculovirus to a specific cell type than said progenitor baculovirus, from which said engineered baculovirus is derived.

13. The genetically engineered baculovirus of claim 10, having a property of more effective evasion of mammalian immune system recognition or inactivation than said progenitor baculovirus, from which said engineered baculovirus is derived.

14. The genetically engineered baculovirus of claim 10, wherein said progenitor virus is a strain of AcMNPV.

15. The genetically engineered baculovirus of claim 10, wherein said envelope protein from Vesicular Stomatitis Virus is VSV-G protein.

* * * * *

UNITED STATES PATENT AND TRADEMARK OFFICE
CERTIFICATE OF CORRECTION

PATENT NO. : 6,607,912 B2
DATED : September 12, 2003
INVENTOR(S) : Blissard et al.

It is certified that error appears in the above-identified patent and that said Letters Patent is hereby corrected as shown below:

Column 19,
Line 19, change "riot" to -- not --.
Line 39, change "farther" to -- further --.

Column 20,
Line 19, change "of" to -- or --.

Signed and Sealed this

Twenty-seventh Day of January, 2004

JON W. DUDAS
*Acting Director of the United States Patent and Trademark Office*